United States Patent [19]
Voigt et al.

[11] 4,321,059
[45] Mar. 23, 1982

[54] PROCESS FOR THE ANALYTICAL DETERMINATION OF HYDROGEN CYANIDE IN GASES

[76] Inventors: Carl Voigt, Rodenbach; Lothar Schmidt, Alzenau-Albstadt; Peter Kleinschmit, Hanau, all of Fed. Rep. of Germany

[21] Appl. No.: 174,829

[22] Filed: Aug. 4, 1980

[30] Foreign Application Priority Data

Aug. 9, 1979 [DE] Fed. Rep. of Germany ....... 2932268

[51] Int. Cl.$^3$ ..................... G01N 31/10; G01N 31/00
[52] U.S. Cl. ................................ 23/232 R; 423/236; 423/352; 252/466 PT
[58] Field of Search ..................... 23/232 R; 422/148; 252/466 PT; 423/355, 354, 352, 236

[56] References Cited

U.S. PATENT DOCUMENTS

| | | | |
|---|---|---|---|
| 2,776,264 | 1/1957 | Dinwiddie et al. | 252/466 PT |
| 2,802,794 | 8/1957 | Sprauer | 252/466 PT |
| 2,817,580 | 12/1957 | Marsh et al. | 423/355 X |
| 3,312,525 | 4/1967 | Schmidt et al. | 423/352 |
| 3,878,289 | 4/1975 | Beavor | 423/236 X |
| 4,148,865 | 4/1979 | Gelbein et al. | 423/236 X |

FOREIGN PATENT DOCUMENTS

| | | | |
|---|---|---|---|
| 1095007 | 2/1959 | Fed. Rep. of Germany | 23/232 R |
| 1406802 | 9/1975 | United Kingdom | 423/236 |

OTHER PUBLICATIONS

Kirk-Othmer, Encyclopedia of Chem. Technology; vol. 4, First Edition, pp. 695-696.
Ullman; Enzyklopadie der technischen Chemie; vol. 9, 4th Ed., pp. 657, 658; vol. 5, 3rd Ed., p. 643; vol. 9 (1957) p. 273; vol. 14 (1963) p. 33.
Gmelin Nitrogen vol. 4, p. 365.

*Primary Examiner*—Kenneth M. Schor
*Attorney, Agent, or Firm*—Cushman, Darby & Cushman

[57] ABSTRACT

Hydrogen cyanide in hydrogen cyanide containing gas is transformed into ammonia by a special iridium catalyst in the presence of at least the equivalent amount of hydrogen for the change. The ammonia is analyzed to provide a measure of the hydrogen cyanide in the hydrogen cyanide containing gas.

16 Claims, 1 Drawing Figure

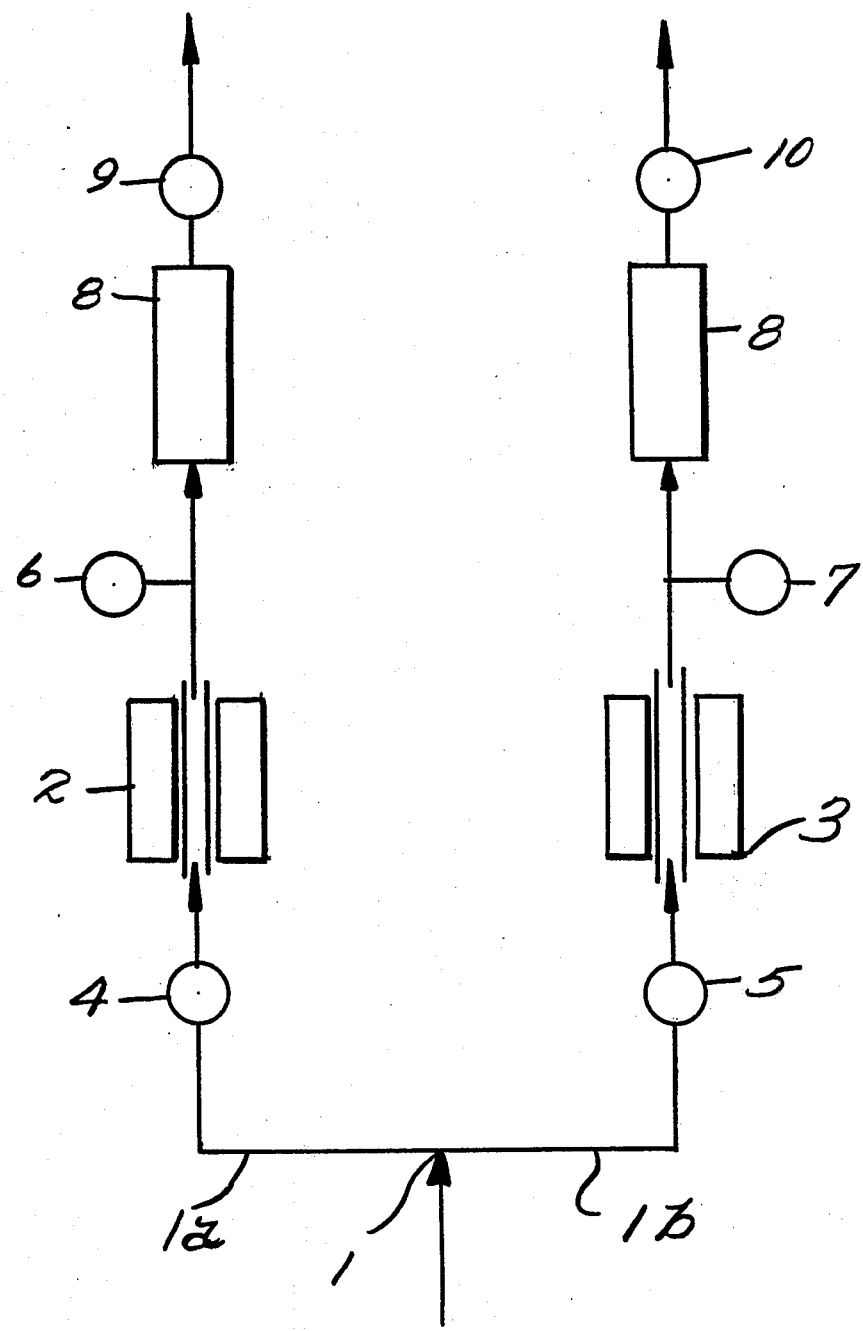

PROCESS FOR THE ANALYTICAL DETERMINATION OF HYDROGEN CYANIDE IN GASES

BACKGROUND OF THE INVENTION

The quantitative and qualitative analysis of hydrogen cyanide in the gas phase which consists essentially of cyanides or other nitrogen containing materials or mixtures of materials is of very great significance, not only for reasons of environmental protection but also with the follow up industrial processes in which hydrogen cyanide is employed as a reactant or the processes in which hydrogen cyanide containing gases are formed.

Previously hydrogen cyanide or cyanides could be determined quantitatively, e.g. through formation of the complex of silver cyanide and titrimetric detection of the end point as silver iodide, see Kirk-Othmer, Encyclopedia of Chemical Technology, Vol. 4, 1st Edition, pages 695-696.

Also specific weight determinations have already been carried out industrially as well as usually qualitatively, hydrogen cyanide determinations in the atmosphere with various test papers, as e.g. the benzidine-copper acetate test or the picric acid-sodium carbonate test (loc. cit.). These types of methods, however, are relatively time consuming and require well trained personnel.

In contrast more favored in use are physical measuring methods, e.g. ultra red spectrometer, gas chromatographs, apparatuses using electrochemical reactions which also are drawn upon for the analysis of hydrogen cyanide, see ACHEMA-Yearbook, 1979.

These physical methods, however, have disadvantages in carrying out in a series since the hydrogen cyanide as is known to polymerize readily, particularly in the presence of basic materials, above all on surfaces made of iron or copper or also on cobalt containing alloys, as well as on glass surfaces or synthetic resin surfaces.

Furthermore, hydrogen cyanide acts corrosively on specific metals which can form the carbide or nitride, as e.g. titanium or molybdenum at elevated temperatures, see Ullmann, Enzyklopedia der technischen Chemie, Vol. 9, 4th Edition, page 657. However, these kinds of metal were frequently used in physical measuring apparatus.

However, a loading of the measuring apparatus or of gas supply parts with polymerizate and/or the partial decomposition of the hydrogen cyanide makes the quantitative detection of the hydrogen cyanide very difficult, if not impossible.

The purpose of the invention therefore is to develop a simple and easily reproducible method of detection for hydrogen cyanide in gases which can also be carried out quantitatively and in series.

SUMMARY OF THE INVENTION

It has now been found that hydrogen cyanide in the gas phase which gas consists essentially of cyanides or other nitrogen containing materials or mixtures of materials can be determined qualitatively and quantitatively, and preferably in series if the hydrogen cyanide containing gas is led at a temperature of 100°-600° C., preferably between 200°-400° C., over an iridium catalyst which is produced by reduction of a hexachloroiridium IV acid on activated aluminum oxide (activated alumina) and in the presence of at least the equivalent amount of hydrogen to change the hydrogen cyanide present into ammonia and the gas drawn off which now contains an amount of ammonia corresponding to the amount of hydrogen cyanide originally present is subjected to a customary physical or physico-chemical method for the determination of ammonia.

The process of the invention is useful for all purposes in which hydrogen cyanide is added, or in which it can be formed.

However, the measuring method of the invention is also suited for the detection of naturally occurring hydrogen cyanide or for its formation from nitrogen containing compounds.

Hydrogen cyanide containing gases occur, e.g. in syntheses of hydrogen cyanide from ammonia and hydrocarbons, with or without the presence of oxygen, according to the known processes, see Ullmann loc. cit., page 657 as well as byproduct in the so-called "Sohio" syntheses, see Ullmann, loc. cit., page 658.

However, the determination of hydrogen cyanide in coke plant, refinery or furnace gases is also of significance, either in the recovery of hydrogen cyanide itself if a separation of the gas pays, e.g. in the separation of saturated choking vapors or for the control of corrosions in portions of plants, see Ullmann loc. cit., 3rd Edition, Vol. 5, page 643; also to protect the environment a control of the hydrogen cyanide content in industrial waste gases is essential.

The necessary amount of hydrogen for the quantitative conversion of the hydrogen cyanide present into ammonia is either partially or entirely present already in the industrial gases, otherwise it must be mixed in before leading the gases under investigation over the catalyst. Preferably there is used a certain excess of hydrogen over the stoichiometric amount. Additional hydrogen if necessary is used in the customarily industrial quality in a given case in admixture with inert gases such as nitrogen.

The required iridium catalyst for the selective transformation of hydrogen cyanide into ammonia is produced in the customary way in the following manner by reduction of hexachloroiridium IV acid on active aluminum oxide, see Ullmann, Enzyklopadie der technischen Chemie, Vol. 14, 1963 page 33 and Vol. 9, 1957, page 273.

Active aluminum oxide in customary form, however, preferably in the form of pellets, is impregnated in the customary manner with an aqueous solution of the above-mentioned hexachloroiridium IV acid and dried at 100°-300° C. in a nitrogen stream and subsequently reduced at 200°-300° C. in a stream of hydrogen. This sequence of impregnation, drying and reduction is generally repeated three to four times. The BET surface area of the active aluminum oxide is between 50 and 250 $m^2/g$ $Al_2O_3$.

With slackening of the activity the catalyst can be regenerated, namely through calcining in oxygen or an oxygen containing gas, preferably in air, for several hours, e.g. 3 to 8 hours, at elevated temperatures of 300°-600° C., whereupon the so calcined catalyst is treated with hydrogen for several further hours, i.e. 3 to 8 hours, at a likewise elevated temperature of 200°-300° C. The catalyst regenerated in this manner still has an activity of 90 to nearly 100% of the starting activity. The activity reached after the regeneration depends first on the size of the previous decrease in catalyst activity and besides on the length and temperature of the calcination and reduction treatment.

A preferred method for the production of the iridium catalyst consists of the following:

10 grams of γ $Al_2O_3$ pellets (97 $m^2$/g surface area, 0.495 kg/l bulk density) were treated with an iridium solution which was produced in the following manner:

13.02 grams of hexachloroiridium-IV-acid hexahydrate
$H_2IrCl_6 \cdot 6H_2O$
having
38.4 weight % Ir, =5 g iridium were treated with 2 ml of concentrated HCl (37 weight %) and the total solution filled up to 48 ml with water.

The solution was used in 8 portions of 6 ml each.

After each impregnation the pellets were preliminarily dried in the drying cabinet at 105° C. for about 20 minutes and subsequently dried for 2 hours at 200° C. in a stream of nitrogen, impregnated again with 6 ml of solution, again dried under the same conditions and subsequently exposed for 2 hours at 250° C. to a gaseous stream of pure hydrogen (moisture free).

This process was repeated at least three to four times.

The catalyst can be employed directly in this form.

For regeneration of the catalyst reduced in its activity the calcination is preferably carried out for 5 hours at 500° C. and the subsequent reduction at 260° C. is carried out by leading 10 liters of hydrogen per hour per gram of catalyst led over the latter.

The gas after the reaction and now containing ammonia can be examined in known manner for its ammonia content.

There can be employed all known physical methods of measurement, see ACHEMA-Yearbook 1979.

If besides hydrogen cyanide there is already simultaneously present ammonia, then the ammonia must be removed quantitatively by customary methods, e.g. by a sulfuric acid absorption, before leading the gases over the iridium catalyst.

In place of sulfuric acid absorption there can also be used a phthalic anhydride prefilter. This prefilter is particularly well suited with very small amounts of ammonia e.g. with <0.5 mol total amount of ammonia.

The process can comprise, consist essentially of or consist of the steps set forth with the stated materials.

The change of hydrogen cyanide to ammonia through hydrolysis in aqueous medium or through reductive splitting is known as of itself (Gmelin, N-Vol. 4, page 365).

Thus, e.g. there is used the hydrolysis of the hydrogen cyanide in the Kjeldahl method for determination of total nitrogen.

However, this method is not suited for the analysis in series because of the long time and well trained personnel required.

It was very surprising that the iridium catalyst used according to the invention was capable of changing hydrogen cyanide selectively and practically quantitatively into ammonia without the formation of disturbing byproducts, through which its determination by modern physical measuring methods becomes possible.

The process can comprise, consist essentially of or consist of the steps set forth with the stated materials.

BRIEF DESCRIPTION OF THE DRAWINGS

The single FIGURE of the drawings diagrammatically shows the apparatus for carrying out the invention.

The invention is further explained in connection with the following examples.

DETAILED DESCRIPTION OF THE INVENTION

EXAMPLE A

In order to demonstrate the selective catalytic activity of the iridium catalyst a starting gas stream which e.g. contains a composition of 22–25 mol % hydrogen cyanide, 3–5 mol % ammonia, 70–75 mol % hydrogen and small amounts of nitrogen, methane and carbon monoxide using the apparatus of the drawing was divided at 1 into two equal gas streams and led via lines 1a and 1b into the two parallel connected furnaces 2 and 3. The measurement of amounts took place in the two rotameters 4 and 5; the pressure was determined in the two manometers 6 and 7. In each furnace there was located a certain tube which in one case was filled with the catalyst to be tested and in the other case remained empty. Subsequently, the unreacted ammonia was absorbed in sulfuric acid and the unreacted hydrocyanic acid was absorbed in aqueous sodium hydroxide at 8 and analyzed according to the customary wet chemical methods. The amount of residual gas was measured at 9 and 10 with customary gas meters. The direct comparison between the tube containing the catalyst and the empty tube demonstrates the activity of the catalyst.

EXAMPLE 1

The iridium catalyst produced in the above-described manner was filled into one of the two ceramic tubes and its decomposition activity measured compared to that of the empty tube. The temperature in both furnaces was 400° C. In all 99.12% of the hydrocyanic acid in the starting gas was converted into ammonia with the aid of the catalyst.

EXAMPLE 2

In a manner analogous to Example I but with a furnace temperature of 300° C. the change of HCN to $NH_3$ took place in an amount of 99.68%.

EXAMPLE 3

A catalyst which after longer use had spent its activity was regenerated in the following manner:

5 hours at 500° C. under air and subsequently 6 hours at 260° C. under hydrogen.

A catalyst regenerated in this manner was tested at 400° C. and there was ascertained thereby a conversion of hydrocyanic acid to ammonia of 99.26%.

COMPARISON EXAMPLE I

The conditions were analogous to Example 1 but there was used a furnace temperature of 25° C. There was not detected any change from HCN to $NH_3$.

COMPARISON EXAMPLE II

Here also the procedure was as in Example 1 but there was used a furnace temperature of 800° C. The transformation of HCN to $NH_3$ was 72.54%.

COMPARISON EXAMPLE III

The experiment was carried out in a manner analogous to Example 1 but employing a furnace temperature of 1000° C. The transformation of HCN to $NH_3$ was 83.2%.

The results from Examples 1-3 were ascertained in several series of experiments and constructed as average values. At 20 ml bulk volume of the catalyst and 100 l of reaction gas per hour the speed-velocity was 500 $h^{-1}$.

EXAMPLE 4

In an analytical determination in order to detect only that portion of the ammonia which is formed through the catalytic decomposition of hydrocyanic acid, in certain cases ammonia present, must be removed in a prefilter. For this purpose with large amounts of ammonia in the starting gas a washing with sulfuric acid is suitable, while smaller amounts suitably are removed with phthalic anhydride, as shown in Example 4.

A stream of gas which in addition to hydrocyanic acid, hydrogen, methane as hydrocarbon, oxygen, and nitrogen also contained ammonia in the range of 5-1000 ppm was led over a prefilter consisting of a glass tube filled with phthalic anhydride. As a result the ammonia present in the gas was completely absorbed while the other components of the gaseous mixture flowed through the prefilter undisturbed.

The entire disclosure of German application P 29 322 68.7-52 is hereby incorporated by reference.

EXAMPLE 5

A stream of gas which in addition to hydrocyanic acid, hydrogen, methane, and nitrogen also contained ammonia in the range of 3-8 mol% was led over a prefilter consisting of a glass tube filled with sulfuric acid 20% by weight. As a result the ammonia present in the gas was completely absorbed while the other components of the gaseous mixture flowed through the prefilter undisturbed.

What is claimed is:

1. A catalytic process for the analytical determination of hydrogen cyanide in a gas comprising contacting a hydrogen cyanide gas with hydrogen and leading the hydrogen cyanide containing gas and hydrogen at a temperature of 100°-600° C. over an iridium catalyst prepared by reducing hexachloroiridium IV acid on active aluminum oxide and reacting at that temperature the hydrogen cyanide with the hydrogen to form ammonia and methane in the presence of the iridium catalyst, the amount of hydrogen being at least the equivalent amount required to convert all of the hydrogen cyanide to ammonia and analyzing the gas drawn off for ammonia to provide a determination of the hydrogen cyanide in the hydrogen cyanide gas.

2. The process of claim 1 wherein the reaction temperature is 200° to 400° C.

3. The process of claim 2 wherein the iridium catalyst used is produced by impregnating active aluminum oxide having a surface area of 50-250 $m^2/g$ with an aqueous solution of a hexachloriridium IV acid, subsequently drying at 100°-300° C. in a stream of nitrogen and then reducing at 200°-300° C. in a hydrogen stream.

4. The process of claim 3 wherein the sequence of impregnation, drying and reducing is repeated at least three times.

5. The process of claim 1 wherein the iridium catalyst used is produced by impregnating active aluminum oxide having a surface area of 50-250 $m^2/g$ with an aqueous solution of a hexachloriridium IV acid, subsequently drying at 100°-300° C. in a stream of nitrogen and then reducing at 200°-300° C. in a hydrogen stream.

6. The process of claim 3 wherein the hydrogen cyanide containing gas initially employed also contains ammonia and the process includes the step of removing this ammonia quantitatively by passing the gas through a filter containing phthalic anhydride before leading the gas over the iridium catalyst.

7. The process of claim 1 wherein the hydrogen cyanide containing gas initially employed also contains ammonia and the process includes the step of removing this ammonia quantitatively by passing the gas through a filter containing phthalic anhydride before leading the gas over the iridium catalyst.

8. The process of claim 3 wherein the hydrogen cyanide containing gas initially employed also contains ammonia and the process includes the step of removing this ammonia quantitatively by absorbing the ammonia in sulfuric acid before leading the gas over the iridium catalyst.

9. The process of claim 1 wherein the hydrogen cyanide containing gas initially employed also contains ammonia and the process includes the step of removing this ammonia quantitatively by absorbing the ammonia in sulfuric acid before leading the gas over the iridium catalyst.

10. The process of claim 1 wherein the gaseous mixture after said contacting consists essentially of (1) hydrogen cyanide and hydrogen or (2) consisting of hydrogen cyanide, hydrogen and at least one other gas selected from the group consisting of nitrogen, methane, carbon monoxide, ammonia, oxygen, and nitrogen.

11. The process of claim 2 wherein the gaseous mixture after said contacting consists essentially of (1) hydrogen cyanide and hydrogen or (2) consisting of hydrogen cyanide, hydrogen and at least one other gas selected from the group consisting of nitrogen, methane, carbon monoxide, ammonia, oxygen, and nitrogen.

12. The process of claim 3 wherein the gaseous mixture after said contacting consists essentially of (1) hydrogen cyanide and hydrogen or (2) consisting of hydrogen cyanide, hydrogen and at least one other gas selected from the group consisting of nitrogen, methane, carbon monoxide, ammonia, oxygen, and nitrogen.

13. The process of claim 1 wherein the gaseous mixture after said contacting consists essentially of hydrogen cyanide, hydrogen, ammonia, nitrogen, methane, and carbon dioxide and the ammonia is removed prior to passing the gaseous mixture over the iridium catalyst.

14. The process of claim 1 wherein the gaseous mixture after said contacting consists essentially of hydrogen cyanide, hydrogen, methane, oxygen, nitrogen, and ammonia and the ammonia is removed prior to passing the gaseous mixture over the iridium catalyst.

15. The process of claim 1 wherein the gaseous mixture after said contacting consists essentially of hydrogen cyanide, hydrogen, methane, nitrogen, and ammonia and the ammonia is removed prior to passing the gaseous mixture over the iridium catalyst.

16. The process of claim 1 wherein the gaseous mixture after said contacting consists essentially of (1) hydrogen cyanide, hydrogen, ammonia and hydrocarbon or (2) hydrogen cyanide, hydrogen, ammonia, hydrocarbon and oxygen.

* * * * *